(12) United States Patent
Pappe et al.

(10) Patent No.: US 11,916,583 B2
(45) Date of Patent: Feb. 27, 2024

(54) SUPPLY SYSTEM FOR ORTHOPEDIC TECHNOLOGY COMPONENTS AND METHOD

(71) Applicant: Otto Bock Healthcare Products GmbH, Vienna (AT)

(72) Inventors: Alexander Pappe, Vienna (AT); Andreas Weigl-Pollack, Goldgeben (AT); Erik Albrecht-Laatsch, Rosdorf (DE); Michael Nolte, Seeburg (DE); Robert Hoffmann, Vienna (AT); Robert Kaitan, Vienna (AT); Luis Sagmeister, Pitten (AT); Thomas Pauser, Steinbrunn (AT); Andreas Schramel, Steinbrunn (AT)

(73) Assignee: OTTO BOCK HEALTHCARE PRODUCTS GMBH, Vienna (AT)

( * ) Notice: Subject to any disclaimer, the term of this patent is extended or adjusted under 35 U.S.C. 154(b) by 92 days.

(21) Appl. No.: 15/733,263

(22) PCT Filed: Dec. 18, 2018

(86) PCT No.: PCT/EP2018/085663
§ 371 (c)(1),
(2) Date: Jun. 18, 2020

(87) PCT Pub. No.: WO2019/121792
PCT Pub. Date: Jun. 27, 2019

(65) Prior Publication Data
US 2021/0099193 A1    Apr. 1, 2021

(30) Foreign Application Priority Data
Dec. 22, 2017    (DE) ...................... 10 2017 131 195.5

(51) Int. Cl.
*A61F 2/70*        (2006.01)
*A61F 5/01*        (2006.01)
(Continued)

(52) U.S. Cl.
CPC .......... *H04B 1/1607* (2013.01); *A61B 90/70* (2016.02); *A61F 2/70* (2013.01); *A61F 5/0102* (2013.01);
(Continued)

(58) Field of Classification Search
CPC ................................................ A61F 2002/702
See application file for complete search history.

(56) References Cited

U.S. PATENT DOCUMENTS 4,443,902 A * 4/1984 Baer ..................... A61G 7/1094
                                                          5/87.1
5,716,330 A * 2/1998 Goldman ................. A61H 1/02
                                                          623/24
(Continued)

FOREIGN PATENT DOCUMENTS

DE    10 2012 015 483 B3    1/2014
KR       10-1690774 B1 *   12/2016 ............... A61F 2/54
(Continued)

OTHER PUBLICATIONS

International Search Report for International Application No. PCT/EP2018/085663, dated Apr. 5, 2019, 10 pages.

*Primary Examiner* — David H Willse
(74) *Attorney, Agent, or Firm* — HOLLAND & HART LLP

(57) ABSTRACT

A supply system for at least one orthopedic technology component, which has at least one electronic and/or electrical device and has a supply connection and/or a radio device for receiving data and/or electrical energy. The supply system also includes a holder for the orthopedic technology component, which has a supply device, and which is compatible with the supply connection and/or the radio device, for supplying the orthopedic technology component with data and/or energy. The invention further relates to a system consisting of a supply system and an orthopedic technology device, and to a method for supplying the system with data and/or energy.

18 Claims, 3 Drawing Sheets

(51) Int. Cl.
  *H02J 7/00*    (2006.01)
  *H04B 1/16*    (2006.01)
  *A61B 90/70*   (2016.01)
  *A61G 5/04*    (2013.01)
  *H04B 1/08*    (2006.01)
  *A61F 2/50*    (2006.01)
  *A61F 2/76*    (2006.01)

(52) U.S. Cl.
  CPC ............ *A61G 5/04* (2013.01); *H02J 7/00034* (2020.01); *H02J 7/0044* (2013.01); *H02J 7/00045* (2020.01); *H04B 1/08* (2013.01); *A61F 2002/5092* (2013.01); *A61F 2002/702* (2013.01); *A61F 2002/705* (2013.01); *A61F 2002/768* (2013.01); *A61F 2005/0155* (2013.01)

(56) References Cited

U.S. PATENT DOCUMENTS

| | | |
|---|---|---|
| 2006/0074493 A1* | 4/2006 | Bisbee, III ................ A61F 2/68 252/62.52 |
| 2015/0066155 A1 | 3/2015 | Haque |
| 2015/0202452 A1 | 4/2015 | Skiera et al. |
| 2015/0351941 A1 | 12/2015 | Bomkamp |
| 2016/0250045 A1 | 9/2016 | Colvin et al. |
| 2019/0105777 A1* | 4/2019 | Dalley ................... B25J 9/1615 |

FOREIGN PATENT DOCUMENTS

| | | | |
|---|---|---|---|
| WO | 20060135851 A2 | 12/2006 | |
| WO | 20100064063 A1 | 6/2010 | |
| WO | WO 2018/004285 A1 * | 1/2018 | ............... A61F 2/54 |

* cited by examiner

SUPPLY SYSTEM FOR ORTHOPEDIC TECHNOLOGY COMPONENTS AND METHOD

CROSS REFERENCE TO RELATED APPLICATIONS

This application is a U.S. National Entry and claims priority to PCT International Patent Application No. PCT/EP2018/085663, filed 18 Dec. 2018, and entitled "SUPPLY SYSTEM FOR ORTHOPAEDIC TECHNOLOGY COMPONENTS AND METHOD", which claims priority to Germany Patent Application No. 10 2017 131 195.5 filed 22 Dec. 2017, the entire disclosures of which are incorporated herein by this reference.

TECHNICAL FIELD

The invention relates to a supply system for at least one orthopedic component which comprises at least one electronic and/or electrical device, to a system consisting of such a supply system and an orthopedic component, and to a method for supplying the orthopedic component.

BACKGROUND

Orthopedic components may in particular be prostheses, ortheses, wheelchairs or parts of prostheses, ortheses or wheelchairs, for example prosthetic or orthetic articulations, tube adapters, prosthetic hands, rotation adapters, prosthetic feet, prosthetic sockets, orthetic rails, orthetic articulations or support boots for a foot and components of wheelchairs, as well as data loggers, radio modules, sensors, feedback elements or storage devices for storing electrical energy.

The equipping of orthopedic components with electrical and/or electronic devices has in the course of development led to improved devices adapted or adaptable to the patient, and has increased. Computer-controlled prostheses, ortheses or other orthopedic components are increasingly being equipped with drives. Likewise, damper devices or other actuators or adjustment devices may be present in order to be able to carry out adaptation to the respective patient, the environmental conditions and/or current movement situations. To this end, sensors are often used, by means of which state information of the patient, of the environment or of the orthopedic component may be recorded. On the basis of the sensor data, by means of stored programs, predetermined modifications are then carried out, characteristic curves are modified, drives are activated or deactivated, or articulations are enabled or blocked.

In order to be able to operate the respective orthopedic component continuously, energy storage units or energy supply devices as well as a control program are often assigned to the orthopedic component. The energy storage units are preferably rechargeable. The control program provides an interface to sensors and external reader devices or data-processing equipment, by means of which the programs executed and/or sensor values recorded may be evaluated, and software updates may optionally be implemented.

The supplying of energy and the data exchange may take place in the fitted state of the orthopedic component in the case of ortheses or prostheses, or during use, for example of wheelchairs. Often, however, the energy and data exchange takes place during phases of nonuse.

SUMMARY

It is an object of the invention to make the data and/or energy exchange or, in general, the maintenance of the orthopedic component more convenient.

According to the invention, this object is achieved by a supply system, by a system and by a method having the features disclosed herein. Advantageous embodiments and refinement of the invention are disclosed in the description and the figures.

The supply system according to the invention for at least one orthopedic component which comprises at least one electronic and/or electrical device and is equipped with a supply connection and/or a radio device for receiving data and/or electrical energy, provides a holder for the orthopedic component, which comprises a supply device, compatible with the supply connection, for supplying the orthopedic component with data and/or energy. Besides positional assignment to the orthopedic component, for example an orthesis, a prosthesis or a wheelchair or parts of an orthesis, prosthesis or wheelchair, which are to be regarded as an orthopedic component, the supply device ensures that data exchange and/or energy exchange, in particular energy supply to an energy storage unit which is assigned to the orthopedic component, can take place during the resting phase or during storage of the orthopedic component on or in the holder. The energy storage unit may be integrated in the orthopedic component or fixed thereto. Data exchange may take place bidirectionally. Recorded data of the orthopedic component may be transmitted to the supply device, in which these data may then be evaluated. Conversely, by the supply device, a software update may be installed, a function test may be carried out or remote maintenance may be activated by the data being transmitted into the orthopedic component. The orthopedic component to this end comprises at least one storage device for data and a processing device or a processor for storing and processing transmitted data.

The electronic and/or electrical device may comprise an electrical load, for example a drive for adjusting constituent parts of the orthopedic component. It is furthermore possible for sensor data to be stored in an electronic device and to be read when the orthopedic component is coupled to the supply device.

The holder may be configured as a storage place or receptacle having at least one fastening device for the orthopedic component, by means of which the orthopedic component can be fixed on the holder. Besides assignment of the orthopedic component to the supply device, a fixed positional assignment of the orthopedic component to the holder is implemented, so that the orthopedic component can always be stored and retrieved at the same position. Particularly in the case of multi-articulation prostheses or ortheses, the positional fixing of the orthopedic component to be holder achieves the effect that the individual constituent parts are kept in a defined assignment to one another even during charging or during supply of the orthopedic component in the unfitted state, so that the orthopedic component may be refitted straightforwardly after the charging of the energy storage unit and the updating of the software.

The fastening device may comprise at least one form-fit element and/or force-fit element, which cooperates with a correspondingly equipped form-fit element or force-fit element on the orthopedic component. In particular, magnets are provided as force-fit elements. Projections, indentations, hook and loop fasteners, clip fasteners, recesses or receptacles configured so as to correspond to the orthopedic component may be provided as a form-fit fastening device. In the case of a conically widening prosthetic socket, the fastening device may comprise a funnel-like receptacle. The fastening device ensures that the orthopedic component remains held securely on the holder during coupling to the supply device.

The supply device and the supply connection may be configured as contactless transmission devices or as a plug and socket, so that, for example, in the case of a contactless transmission device energy and data are transmitted inductively or capacitively or by radio. In the case of contacted transmission of energy and/or data a plug connection is provided, which may also be configured to be self-aligning. The plug connection comprising a plug and a socket may be provided with form-fit elements and/or force-fit elements in order to allow self-alignment and therefore centering of the plug and the socket with respect to one another.

Encoding, which can be read by means of an identification device arranged in or on the holder, may be stored in the orthopedic component. Conversely, an identification device, by means of which encoding arranged in or on the holder can be read, may be arranged in the orthopedic component. There is therefore the possibility of mutual authentication of the holder and the orthopedic component. Furthermore, a plurality of parts of an orthopedic component may be equipped with electrical and/or electronic devices, for example a prosthetic knee articulation and a prosthetic ankle articulation in the case of a leg prosthesis, or a prosthetic elbow articulation and an actuatable prosthetic hand in the case of an arm prosthesis. Each of these parts of the orthopedic component may be equipped with specific encoding, so that all the encodings of electrical and/or electronic components may be read by the holder. By the mutual authentication of the holder and the orthopedic components and parts thereof, it is possible to modify the scope and the nature of the energy transmitted or data transmitted. It is therefore possible to provide one holder for a plurality of orthopedic components. Each holder may identify the orthopedic component assigned to it and, according thereto, transmit or read the required amount of energy, type of energy and control programs, data or the like.

A cleaning apparatus may be arranged on the holder, in order to be able to clean the orthopedic component during the data exchange or the energy supply and prepare it for further use. The cleaning apparatus may comprise a UV source, a plasma generator and/or an X-ray tube, in order to clean or disinfect the orthopedic component by corresponding irradiation or ionization. In particular, such an integrated cleaning apparatus is advantageous in the case of orthopedic components worn directly on the skin.

The invention likewise relates to a system consisting of a supply system as described above and an orthopedic device that can be supplied with data and/or energy by means of the supply system. Configuring the supply system and the orthopedic device as an overall system facilitates the mutual matching and the smooth and trouble-free supply with data and/or energy.

The method for supplying an orthopedic component with data and/or energy, the orthopedic component comprising at least one electronic and/or electrical device and being equipped with a supply connection for receiving data and/or electrical energy, provides that the orthopedic component is fastened in or on a holder, in or on which a supply device, compatible with the supply connection, for supplying the orthopedic component with data and/or energy is arranged, that the supply connection is coupled to the supply device and data and/or energy transmission takes place automatically following coupling of the supply device to the supply connection. As soon as the orthopedic component is stored in the holder and placed on the holder, data maintenance and possibly required energy transmission take place. Before the data and/or energy transmission, identification of the orthopedic component may take place, for example by interrogating an encoding of the at least one orthopedic component or all the orthopedic components or parts of orthopedic components having a plurality of electronic and/or electrical devices.

Matched data may then be transmitted and a functional test may be instigated, as a function of the orthopedic component. In the case of a function test, the entire functional scope of the orthopedic component may be tested; for example, maximum tilting of elements of the orthopedic component with respect to one another may be initiated and a test may be carried out as to whether the maximum displacement travel and tilting range is reached. Adjustments of resistances as well as other functional tests may also be carried out during the supplying of the orthopedic component with data and/or energy.

After the coupling of the supply device to the supply connection of the orthopedic component, a mode switchover of the orthopedic component may be carried out. After the coupling to the supply device, switchover takes place from an operating mode into a supply mode, in which some functions are turned off and others are activated in order to prevent the function test from being carried out in the fitted state of the orthopedic component or during actual use.

Additional functions may be activated in the supply mode; for example, music may be played in order to make the waiting time until reuse of the orthopedic component as pleasant as possible.

The use of mutual authentication prevents false data from being transmitted or safety-relevant functions or a source code being read and manipulated.

BRIEF DESCRIPTION OF THE DRAWINGS

The exemplary embodiments will be explained in more detail below with the aid of the appended figures, in which.

DETAILED DESCRIPTION

Figure 1:
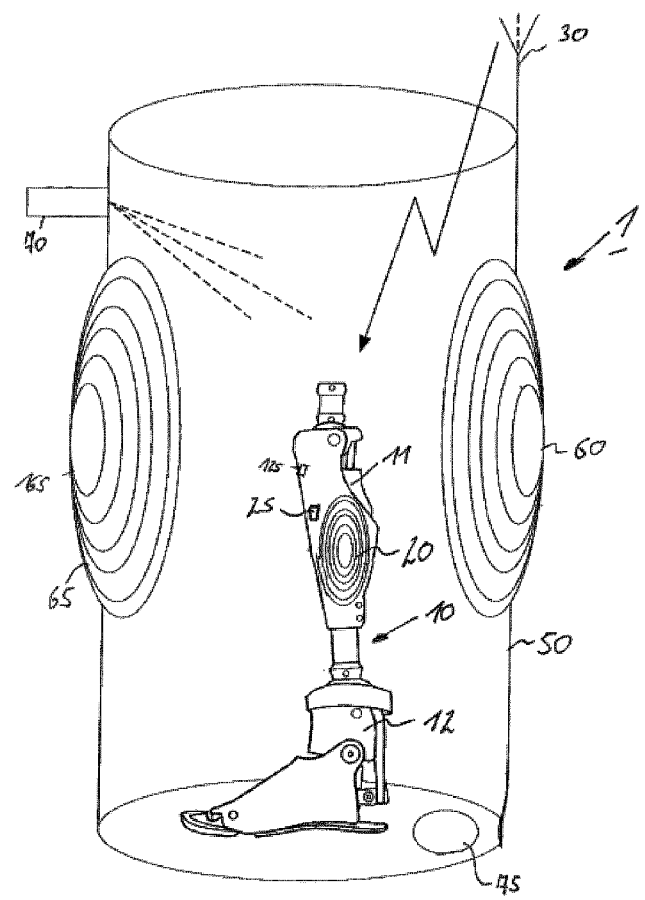
FIG. 1 shows a first embodiment of a supply system for a prosthesis of a lower extremity.

FIG. 1 represents a schematic representation of a supply system 1 for an orthopedic component 10 in the form of a prosthesis for a lower extremity. The orthopedic component 10 comprises a prosthetic knee articulation having a lower leg component, an electronically controlled knee articulation and a prosthetic foot. A plurality of electronic devices 11, 12, which are essential for the desired functionality of the orthopedic component 10, are arranged on the orthopedic component 10. Arranged in the lower leg component, there is a computer-controlled hydraulic actuator which, besides control devices, is assigned sensors, drives for valves or pumps and an energy storage unit, by means of which a relative movement between an upper part, for example a connection for a prosthetic socket, and the lower leg component is controlled distally with respect to the articulation axis. The movement resistances in terms of extension and flexion may be modified by means of the electronic controller 11.

Arranged in the region of the ankle articulation, there is also a further electrical and/or electronic device 12, by means of which the flexion and extension resistances of the foot part relative to the lower leg component can be adjusted. As an alternative or in addition, drives are arranged in the electrical and/or electronic devices 11, 12. Arranged on the orthopedic component 10, there is a supply connection 20, by means of which data and/or electrical energy may be received or input, so that both the data and the electrical energy may be stored and processed inside the orthopedic component 10. In the exemplary embodiment represented, the supply connection 20 is configured as a wireless supply connection, for example a coil device, in order to transmit energy by using induction. Furthermore, a radio device for receiving data may be provided, in order to input and store information, for example a software update.

Encoding 25, by means of which the orthopedic component 10 can be uniquely identified, is likewise stored on the orthopedic component 10. The encoding 25 may be stored in a transponder, transmitter and/or a readable storage device, or it may be arranged on the orthopedic component 10 as a barcode, QR code or other marking. The orthopedic component is located in a holder 50, which in the exemplary embodiment represented is schematically configured as a cylindrical holder, which comprises a bottom in which an opening 75 is arranged as an outlet. A cleaning apparatus 70, which may be configured as a UV source, as a plasma generator, as a shower or washing device or as an X-ray tube, is arranged on the holder 50. In principle, it is possible to arrange a plurality of cleaning apparatuses 70, including ones that are different from each other, on a holder 50. If the cleaning apparatus 70 is configured as a shower device having a pump and a spray element for spraying cleaning liquids, excess cleaning liquid may flow out through the drain 75. The orthopedic component 10 may be positioned in the holder 50 via an upper opening. The upper opening may be closable by means of a lid. The wall may be at least partially transparent or equipped with a window.

An antenna 30, by means of which on the one hand data may be received and on the other hand data may be transmitted to the radio device, is arranged on the holder 50. This is indicated by the arrow. The antenna 30 is part of the radio device 30 or of a supply device 60, which are arranged on an outer wall of the holder 50 and on the orthopedic component 10, by means of which data are transmitted via the antenna 30 to the orthopedic component 10 and to the electrical and/or electronic devices 11, 12. Likewise arranged on the holder 50 is an identification device 65, by means of which the encoding 25 of the orthopedic component 10 can be read. The encoding 25 may be recorded purely optically and identified by means of image evaluation. As an alternative or in addition, the transponder may be excited by the encoding 25 and read. Likewise, a transmitter may transmit the encoding 25 continuously or at time intervals, and the signal may be received and evaluated by the identification device.

As an alternative or in addition, an identification device 125, by means of which an encoding 165 arranged in or on the holder 50 can be read, may be arranged or integrated on or in the orthopedic component 10. By means of the respective identification device 65, 125 and encoding 25, 165, it is possible to match the respective holder 50 to the orthopedic component 10 arranged in it and to establish and adapt the way in which energy and data are transmitted, and in particular the amount of energy and types of data which are transmitted.

In the exemplary embodiment represented in FIG. 1, the orthopedic component 10 is only deposited in the holder 50. For example, a receptacle or a fastening element may be arranged on the bottom of the holder 50 in order to fix the orthopedic component 10 in the holder 50. This may for example be done by means of form-fit elements, hook and loop fasteners, snap fasteners, tabs, straps, projections, hooks or else magnets.

Figure 2:
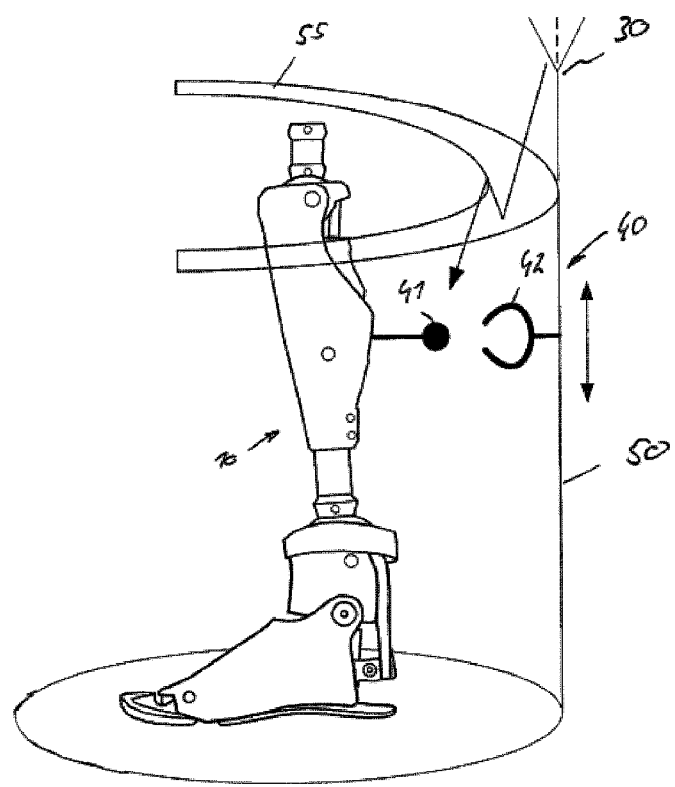
FIG. 2 shows a second embodiment of the supply system.

FIG. 2 shows a variant of the holder 50 which likewise comprises a bottom and a side wall. A frame is arranged on the upper end of the holder 50 in order to form an upper barrier, for example for leaning or depositing the orthopedic component 10. Unlike in FIG. 1, in the embodiment according to FIG. 2 besides wireless data transmission via the antenna 30, mechanical coupling by means of a fastening device 40 is provided, with which a first form-fit component 42 is arranged height-adjustably on the holder 50. The adjustability, in particular displaceability, is indicated by means of the double arrow. By means of the height adjustability, it is possible to receive different orthopedic components 10 in a holder 50. Arranged on the orthopedic component 10, there is a corresponding form-fit element 41 which is configured for energy transmission besides mechanical latching with the corresponding form-fit element 42 and the holding function thereby implemented. This means that the two form-fit elements 41, 42 are configured as a plug and socket and therefore simultaneously provide mechanical latching and electrical contacting. Besides pure energy transmission, data transmission may additionally take place as well via the contacting by means of the form-fit elements 41, 42.

Figure 3:
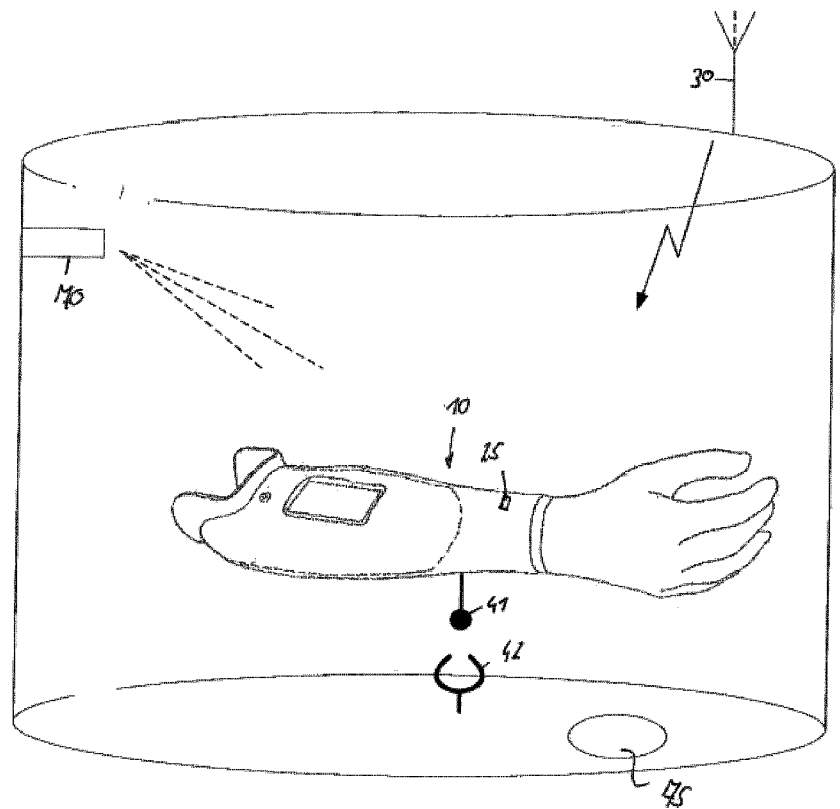
FIG. 3 shows a supply system for a prosthesis of an upper extremity.

FIG. 3 represents a variant of FIG. 1, in which a prosthesis for an upper extremity is arranged as an orthopedic component 10 inside the holder 50. By means of the two form-fit elements 41, 42, the orthopedic component 10 is held in a defined position inside the holder 50. A cleaning apparatus 70 is likewise arranged on the holder 50 in order to be able to clean the orthopedic component 10 after it has been deposited.

We claim:

1. A supply system for at least one orthopedic component, the supply system comprising:
   at least one electronic device;
   at least one of a supply connection and a radio device for at least one of receiving data and electrical energy;
   a holder for the orthopedic component;
   a supply device, compatible with the at least one of the supply connection and the radio device, for supplying the orthopedic component with at least one of data and energy, wherein after the orthopedic component is coupled to the supply device, a mode switchover of the orthopedic component from an operating mode to a supply mode is carried out, wherein, as a function of the orthopedic component, data adapted to the orthopedic component are transmitted from the supply device to the supply connection in the supply mode, wherein, in the operating mode, initiation of a function test in a fitted state of the orthopedic component is prevented, and wherein, in the supply mode, some functions of the orthopedic component are turned off and some functions of the orthopedic component are activated to initiate the function test of the orthopedic component in an unfitted state, and wherein the function test of the orthopedic component is only performed in the unfitted state.

2. The supply system as claimed in claim 1, wherein the holder is configured as a storage place or receptacle having at least one fastening device, the at least one fastening device fixing the orthopedic component on the holder.

3. The supply system as claimed in claim 2, wherein the at least one fastening device comprises at least one of at least one form-fit element and at least one force-fit element, which cooperates with a correspondingly equipped form-fit element or force-fit element on the orthopedic component.

4. The supply system as claimed in claim 1, wherein the supply device and the supply connection are configured as contactless transmission devices or as a plug and socket.

5. The supply system as claimed in claim 1, further comprising encoding, which can be read by an identification device arranged in or on the holder, is stored in the orthopedic component, and an identification device, which is configured to read the encoding arranged in or on the holder, is arranged in the orthopedic component.

6. The supply system as claimed in claim 1, wherein a cleaning apparatus is arranged on the holder.

7. The supply system as claimed in claim 6, wherein the cleaning apparatus comprises at least one of a UV source, a plasma generator, and an X-ray tube.

8. A system comprising a supply system as claimed in claim 1 and the at least one orthopedic component.

9. A method for supplying an orthopedic component with at least one of data and energy, the orthopedic component comprising at least one electronic device and being equipped with at least one of a supply connection and a radio device for receiving the at least one of data and electrical energy, the method comprising:
fastening the orthopedic component in or on a holder, in or on which a supply device, compatible with the at least one of the supply connection and the radio device, for supplying the orthopedic component with the at least one of data and energy is arranged, the at least one of the supply connection and the radio device is coupled to the supply device and transmission of the at least one of data and energy takes place automatically, wherein after the coupling to the supply device, a mode switchover of the orthopedic component from an operating mode to a supply mode is carried out, wherein, as a function of the orthopedic component, data adapted to the orthopedic component are transmitted from the supply device to the supply connection in the supply mode, wherein, in the operating mode, initiation of a function test in a fitted state of the orthopedic component is prevented, and wherein, in the supply mode, some functions of the orthopedic component are turned off and some functions of the orthopedic component are activated to initiate the function test of the orthopedic component in an unfitted state, and wherein the function test of the orthopedic component is only performed in the unfitted state.

10. The method as claimed in claim 9, wherein identification of the orthopedic component is carried out before transmission of the at least one of data and energy.

11. A supply system for at least one orthopedic component, the system comprising:
at least one electronic device;
a supply connection or a radio device for receiving data or electrical energy;
a holder for the orthopedic component;
a supply device compatible with the supply connection or the radio device, the supply device supplying the orthopedic component with data or energy, wherein after the orthopedic component is coupled to the supply device, a mode switchover of the orthopedic component from an operating mode to a supply mode is carried out, wherein, as a function of the orthopedic component, data adapted to the orthopedic component are transmitted from the supply device to the supply connection in the supply mode, wherein, in the operating mode, initiation of a function test in a fitted state of the orthopedic component is prevented, and wherein, in the supply mode, some functions of the orthopedic component are turned off and some functions of the orthopedic component are activated to initiate the function test of the orthopedic component in an unfitted state, and wherein the function test of the orthopedic component is only performed in the unfitted state.

12. The supply system as claimed in claim 11, wherein the holder is configured as a storage place or receptacle having a fastening device, the fastening device fixing the orthopedic component on the holder.

13. The supply system as claimed in claim 12, wherein the fastening device comprises a form-fit element or a force-fit element, which cooperates with a correspondingly equipped form-fit element or force-fit element on the orthopedic component.

14. The supply system as claimed in claim 11, wherein the supply device and the supply connection are configured as contactless transmission devices or as a plug and socket.

15. The supply system as claimed in claim 11, an identification device arranged on the holder and stored in the orthopedic component, the identification device configured to read encoding.

16. The supply system as claimed in claim 11, wherein a cleaning apparatus is arranged on the holder.

17. The supply system as claimed in claim 16, wherein the cleaning apparatus comprises a UV source, a plasma generator, or an X-ray tube.

18. A system comprising the supply system claimed in claim 11 and the at least one orthopedic component.

* * * * *